US007067678B2

(12) United States Patent
Scialdone (10) Patent No.: US 7,067,678 B2
(45) Date of Patent: Jun. 27, 2006

(54) DERIVATIVES OF DIHYDRONEPETALACTONE AND METHOD FOR PREPARATION

(75) Inventor: Mark A. Scialdone, Oxford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 7 days.

(21) Appl. No.: 10/997,279

(22) Filed: Jul. 1, 2005

(65) Prior Publication Data

US 2005/0239875 A1    Oct. 27, 2005

Related U.S. Application Data

(60) Provisional application No. 60/525,304, filed on Nov. 26, 2003.

(51) Int. Cl.
*C07D 311/94* (2006.01)
*A01N 43/16* (2006.01)

(52) U.S. Cl. ...................... 549/283; 514/456
(58) Field of Classification Search ............... 549/283; 514/456
See application file for complete search history.

(56) References Cited

FOREIGN PATENT DOCUMENTS

WO    WO 03/084946 A1    10/2003

OTHER PUBLICATIONS

Eisenbraun, et al., "Structure of Nepetalic Acid in the Solid State an in Solution by X-ray Diffraction and Nuclear Magnetic Resonance Analysis", J. Org. Chem. (1981), pp. 3302-3305, vol. 46, Oklahoma.
McElvain, et al., "The Constituents of the Volatile Oil of Catnip. I. Nepetalic Acid, Nepetalactone and Related Compounds", J. Chem. Soc., (1941), pp. 1558-1563, vol. 63, Wisconsin.
Dawson, et al., "The Aphid Sex Pheromone Cyclopentanoids: Synthesis in the Elucidation of Structure and Biosysnthetic Pathways", Bioorganic & Medicinal Chemistry (1996), pp. 351-361, vol. 4, No. 3, Great Britain.
Eisenbraun, et al., "(4aS, 7S, 7aR)", et al., J. Org. Chem. (1988), pp. 3968-3972, vol. 53, California.
Hiromichi Ohta et. al., Regiospecific Introduction of Two Carbon Moieties into the Vicinal Positions of Cyclopentadiene and Synthesis of C9-Terpene Lactones, J. Org. Chem., 1977, pp. 1231-1235, vol. 42.
International Search Report Dated Jun. 3, 2005, International Application No. PCT/US2004/039511, Filing Date: Nov. 24, 2004.

*Primary Examiner*—Bernard Dentz (57) ABSTRACT

3-substituted dihydronepetalactone is prepared by deprotonation of nepetalactone and treatment with Grignard reagent to form alkyl and aryl substituted compounds. The compounds so prepared are odorous and have a wide range of utility ranging from insect repellents to fragrance compounds, such as perfumes, among others.

20 Claims, 5 Drawing Sheets

Figure 3 Results of Example 15

Figure 4: Results of Example 16

Figure 5: Results of Example 17

DERIVATIVES OF DIHYDRONEPETALACTONE AND METHOD FOR PREPARATION

This application claims the benefit of U.S. Provisional Application No. 60/525,304, filed on Nov. 26, 2003.

FIELD OF THE INVENTION

The present invention is directed to derivatives of dihydronepetalactone, which are useful as fragrance compounds, to impart, for example, a desirable or attractive fragrance to objects, and are also useful as insect repellents. The present invention is also directed to a method for preparing derivatives of dihydronepetalactone, which method is particularly well-suited for transforming naturally occurring nepetalactone to the desired derivative.

BACKGROUND OF THE INVENTION

Dihydronepetalactone (DHN) is an iridoid monoterpenoid that may be represented schematically by the structure of Formula II,

II and has been described by Hallahan in US 2003/0191047 (which is incorporated in its entirety as a part hereof for all purposes) as possessing a fragrance that many humans find attractive, and thus as having usefulness as a fragrance compound. Hallahan, in WO 03/079786 (which is incorporated in its entirety as a part hereof for all purposes), has also disclosed that DHN compares favorably as an insect repellent with N,N-diethyl-m-toluamide (DEET), which has been the insect repellent of choice in most commercially available insect repellents. DHN may be prepared by the catalytic hydrogenation of nepetalactone.

Various derivatives of DHN are known, among which, for example, is nepetalic acid, which may be represented schematically by the structure of Formula III,

III

Nepetalic acid may be isolated from the essential oil of nepeta cataria [see, for example, Eisenbraun et al, J. Org. Chem., 53(17), 3968–3972 (1988)]. Eisenbraun also teaches the treatment of nepetalic acid with an oxidizer and base to produce a dicarboxylic acid ring-opened structure (nepetalinic acid).

Nepetalic acid (Formula III) may also be beneficially synthesized by treatment of nepetalactone with strong base according to the method of McElvain et al in J. Am. Chem. Soc., 63, 1558–1563 (1941). The structure of Formula III was confirmed by Eisenbraun et al in J. Org. Chem. 46, 3303–3305 (1981).

Another derivative of DHN, as disclosed in Dawson et al, Bioorganic and Medicinal Chemistry, 4 (3), 351–361 (1996), is the ethoxy substituted variation of the structure of Formula III, represented by the structure of Formula IV

IV

According to Dawson, op. cit., the compound of Formula IV is prepared as an intermediate in a synthetic pathway presented therein for preparing nepetalactone from R-pulegone.

In the references noted above, the respective derivatives of DHN disclosed therein are not described as being useful as insect repellents or for purposes related to fragrance, aroma or odor.

Nepetalactone, represented schematically in structure of Formula I,

I is a major component of an essential oil secreted by plants of the genus Nepeta, and is the active ingredient in catnip. Although the aroma of nepetalactone is generally considered unpleasant by humans, cats find it attractive. Nepetalactone may also play a role as an insect repellent as studies of the repellency of catnip oil (predominantly nepetalactone) have shown that it was repellent towards a number of insect species on short-term exposure, but not to a number of other species [Eisner, T., Science 146:1318–1320 (1964)].

While nepetalactone and DHN are both compounds that have exhibited some degree of usefulness as an insect repellent, only DHN of the two presents a pleasing odor to humans. It is thus difficult to predict which member of the iridoid monoterpenoid family of compounds will or will not have any particular property or utility.

A need nevertheless remains to develop new compounds that will be useful as insect repellents but that will have other uses as well, some of which uses may be based on fragrance, aroma and odor. Applicants have discovered previously unknown compounds that are derivatives of DHN, and that have usefulness as insect repellents in addition to other uses based on fragrance, aroma and/or odor.

SUMMARY OF THE INVENTION

The present invention provides for a compound represented schematically by the structure of Formula (V)

where R is alkyl or aryl.

The present invention further provides for a process to prepare a compound of Formula V comprising contacting nepetalic acid with a base, and with a Grignard reagent; or with only a Grignard reagent.

This invention also provides for a variety of compositions that include the compound of Formula V such as a composition that includes a mixture of different compounds according to Formula V, or a composition that includes a compound of Formula V and one or both of an adjuvant and a carrier.

This invention further provides for a perfumed or insect-repellent composition of matter or article of manufacture that includes a compound of Formula V; and thus correspondingly provides a method of making a perfumed or insect-repellent composition of matter or article of manufacture by forming the composition from, or incorporating into the article, a compound of Formula V.

In particular, this invention further provides a topical treatment for skin, such as a fragrance or perfume composition, or an insect repellent, that includes a compound of Formula V.

This invention further provides a method of treating skin or fur by applying to the skin or fur a compound of Formula V, or a composition including a compound of Forumla V. The invention thus also provides a method of repelling one or more insects by exposing the insect(s) to a compound of Formula V.

DETAILED DESCRIPTION OF VARIOUS PREFERRED EMBODIMENTS

The present invention provides an entirely new class of highly odorous bicyclic lactones useful variously as insect repellents and for other purposes related to fragrance, aroma and/or odor of the compound.

The compounds described herein will be recognized as exhibiting stereoisomerism, both enantiomerism and diastereomerism as the case may be. Unless a specific stereoisomer is indicated, the discussion will be understood to refer to all possible isomers, whether the structures are shown in the stereochemically ambiguous form of the structures of Formulae I–V, or are shown as a specific stereoisomer (as in various locations hereinbelow) when other stereoisomers are also possible. There are numerous instances in which the discussion may focus on a specific stereoisomer of a diastereomeric pair (such as a case where, of several stereoisomers of identical chemical content, certain members of the group have differing chemical properties or biological activity), and this will also be specifically noted.

The present invention provides for the compounds that may be represented schematically by the structure of Formula V, where R is alkyl or aryl.

While there is in principle no limitation on the type of alkyl or aryl groups that are useful in the practice of the invention, there will be practical considerations as to the size of the R substituent that would have practical use in commerce. Furthermore, it may be desirable to avoid incorporating highly reactive functionality in the R substituents to avoid side reactions.

In addition to practical considerations associated with synthesis, it will be recognized that, for end-uses where odor is a key factor, the higher molecular weight members of the class of compounds of this invention will generally exhibit lower respective vapor pressures under the same conditions than the lower molecular weight members of the class, and therefore may be less preferred in those kinds of circumstances.

In view of those considerations, representative values for R may include normal or branched $C_1$–$C_{20}$ alkyl such as sec-butyl or neo-pentyl, and is preferably normal $C_1$–$C_{12}$ alkyl such as methyl, ethyl, propyl, butyl, pentyl or hexyl; or R may be substituted or unsubstituted $C_6$–$C_{20}$ phenyl, and is preferably unsubstituted or meta- or para-substituted phenyl, where the substituent on phenyl may be normal $C_1$–$C_{12}$ alkyl or alkoxy, or halogen. Most preferably, R is methyl or ethyl, phenyl, or para- or meta-tolyl.

A compound according to this invention includes a compound that is a single stereoisomer as well as a compound that is a mixture of stereoisomers. A composition may be formed from a mixture of the compounds of this invention in which R, as described above, differs among the various compounds from which the composition is formed.

In the process of this invention, the compound represented schematically by the structure of Formula V is prepared from nepetalic acid by deprotonation, followed by treatment with Grignard reagent.

The nepetalic acid starting material is preferably prepared from nepetalactone according to the teachings of McElvain supra. The nepetalactone bicyclic structure can exist in any of four stereoisomeric forms, as shown in the structures of Formulae VIIa~VIId.

VII

Nepetalactone extracted from the essential oil of the *nepeta* (catmint) plant leaves is a preferred source of raw material as nepetalactone is present in large quantity therein and may be readily purified therefrom. This produces a highly desirable route from a natural product to the compounds of the invention. Fractional distillation has been found to be an effective method for both purifying nepetalactone from the essential oils, and for separating the several stereoisomers from one another. Chromatographic separations are also suitable.

Only the first three listed stereoisomers of nepetalactone exist in the essential oil of the *nepeta cateria* plant. Cis, trans nepetalactone is the predominant isomer that may be isolated from the *nepeta cateria* plant and is therefore the most useful because of availability. Other plant species have been identified that have essential oils enriched with the trans, cis and cis, cis nepetalactone isomers.

Following the method of McElvain et al, op. cit., the starting nepetalic acid suitable for use in the process of this invention is prepared by hydration of nepetalactone with strong base to produce nepetalic acid. In the hydration of cis, trans nepetalactone, there exists the possibility of obtaining 4 diastereomers of nepetalic acid as shown schematically in structures of Formulae VIa~VId.

VI

The structures depicted in Formulae VI are diastereomeric pairs at C3 (the lactol) and C4 (the methyl proximate to the lactol). Eisenbraun et al, *J. Org. Chem.* 46, 3303–3305 (1981), showed that the absolute stereochemistry of the major nepetalic acid diastereomer that is crystallized from this product mixture is structure VIa. Spectral evidence and the solved single crystal x-ray structure indicate that the cyclic lactol tautomer VIa exists as a single diastereomer with respect to the methyl-bearing asymmetric carbon (C4) adjacent to the lactol carbon. Crystallization unambiguously sets the relative (and thus absolute) stereochemical configuration of the methyl group at C4 such that the methyl occupies an equatorial configuration.

When trans, cis nepetalactone is subjected to hydration, the ring-opened tautomer is obtained as a diastereomeric pair:

Cis, cis-nepetalactone and trans, trans nepetalactone are also suitable for use in preparing nepatalic acid by hydration.

After the preparation of nepetalic acid, it is treated with a non-aqueous base in a deprotonation step to form a carboxylate salt. In one embodiment, for example, the nepetalic acid is treated with an alkali metal hydride, preferably KH. In this embodiment, the deprotonation step is followed by treatment with Grignard reagent to form a product represented schematically by the structure Formula V. Typical Grignard reagents include, but are not limited to, those that are prepared by the union of metallic magnesium with an organic chloride, bromide or iodide usually in the presence of ether and in the complete absence of water.

In a preferred embodiment, the nepetalic acid is derived from cis, trans nepetalactone with the result that the product created by the above described steps may be represented schematically by the structure Formula VIII, with the absolute stereochemistry of the anti product shown.

VIII

Both the anti- and syn-addition products may be formed, and the relative amounts in which the two products are formed is governed primarily by steric factors resulting from the choice of Grignard reagent, as discussed in more detail below.

As previously discussed, nepetalic acid may, in an alternative embodiment, be derived from trans, cis nepetalactone, thereby forming the nepetalic acid tautomer consisting of the diastereomeric pair shown above. As a consequence, in this embodiment, treatment of that tautomer pair with an alkali metal hydride, preferably KH, followed by treatment with Grignard reagent results in production of the diastereomeric mixture represented schematically by the structures of Formulae IXa–IXb.

IX a    b

Although this particular embodiment of the process started with trans, cis nepetalactone, the final product is in the cis, trans configuration. Shown in IX are only the anti products. Both the anti- and syn-addition products may be formed, however, and the relative amounts in which the two products are formed is governed primarily by steric factors resulting from the choice of Grignard reagent, as discussed in more detail below.

Very reactive metal hydrides such as lithium aluminum hydride may be too reactive for use in the deprotonation step. Such species may reduce the lactone, which would not be desirable, and are therefore less preferred.

In a further, preferred, embodiment, the nepetalic acid is treated with more than one equivalent of Grignard reagent, and preferably at least two equivalents of Grignard reagent to effect formation of the products, such as those depicted respectively in the structures of Formulae VIII and IX. This embodiment of the process of the invention eliminates the step of first treating nepetalic acid with a separate non-aqueous base such as an alkali metal hydride. Use of an amount of Grignard reagent in slight excess of two equivalents ensures high conversion to the desired product.

Suitable for use in the process herein disclosed are any Grignard reagents that are reactive with aldehydes including but not limited to alkyl magnesium chlorides, alky magnesium bromides, aryl magnesium chlorides, and aryl magnesium bromides. Also included are dialkylzincs, diarylzincs and alkyllithiums and aryllithiums. Representative substituents that may be present on suitable Grignard reagents include methyl, ethyl, n-propyl, butyl, pentyl, hexyl phenyl, para- and meta-substituted phenyl including para- and meta-tolyl, and para-methoxy-phenyl.

While there is no specific limitation on the choice of Grignard reagents suitable for the practice of the invention, some Grignard reactions are more effective than others at generating products that are high in purity in terms of stereochemistry. While not wishing to be bound by any theory, it is believed that steric factors govern the relative rates of production of the anti- and syn-configured isomers produced by the treatment of nepetalic acid with base and/or Grignard reagent, such as those shown in the structures of Formulae VIII and IX. The larger the organic radical of the Grignard reagent, the greater the tendency is to form predominantly anti-configured product. Small organic radicals on the other hand are not sterically hindered, and the anti-configured product is thus not energetically favored over the syn-configured product.

It has been found that the smaller the alkyl group on a Grignard reagent, the less diastereroselective the addition reaction is. Methyl, ethyl, and n-propyl Grignard show no diastereoselectivity, forming a 1:1 mixture of anti-addition product and syn-addition product. Branched alkyls such as isopropyl and sec-butyl, or cyclic alkyl such as cyclohexyl provide lower yields of the final products than do the comparable linear alkyls.

By contrast, phenyl Grignard is completely diastereoselective for the anti-addition product. In particular, para-substituted phenyl Grignard reagents like p-tolyl Grignard, give exclusively the anti products with excellent 1,2-asymmetric induction from the established methyl-bearing C4. Conversely, ortho-substituted phenyl Grignard reagents are less diastereoselective in this reaction, resulting in some syn product and thus a diastersomeric mixture. The governing mechanism may be related to the extent to which the given reactants follow the Felkin-Anh rules, such rules being known in the art.

Aryl Grignard reagents are diastereoselective and provide 3-substituted dihydronepetalactones, whose absolute stereochemistry is consistent with the structural representation of the embodiments depicted in Formula VIII. This is illustrated in the examples where it is observed that p-tolylmagnesium bromide gave only one diastereomer (as verified by single crystal x-ray and NMR analysis in Example 2) while methylmagnesium bromide gave a 1:1 inseparable mixture of diastereomers (in Examples 3 and 4). Many 3-substituted dihydronepetalactones can be prepared by the process of this invention.

In one aspect of the invention, it is found that meta-substituted phenyls such as meta-tolyl give lactone products that are oils. The oils so formed performed better in the insect repellency tests described hereinbelow than did the lactones obtained from phenyl and para-tolyl which gave more crystaline products such as para-tolyl.

In the processes described above, the steps of adding base and then Grignard reagent, or of adding Grignard reagent in one or more increments, may be performed at a temperature in the range of about 25 C to about to −78 C, with a temperature in the range of 5 C to −5 C being preferred to prevent decomposition during this step The compounds of this invention are directed to use for a multiplicity of purposes, such as use in an effective amount for the repellency of various insect species, or in a perfume composition or in a topical treatment for skin. For example, the compounds hereof may be applied in a topical manner to human or animal skin, fur or feathers, or to growing plants or crops, to impart insect repellency or a pleasant odor or aroma.

Desirable properties of an insect repellent include low toxicity, resistance to loss by water immersion or sweating, low or no odor or at least a pleasant odor, ease of application, and rapid formation of a dry tack-free surface film on the surface of the host to which applied. In order to obtain these properties, the formulation for a topical insect repellent should permit insect-infested animals (e.g., dogs with fleas, poultry with lice, cows with ticks, and humans) to be treated with an insect repellent by contacting the skin, fur or feathers of such an animal with an effective amount of the repellent for repelling the insect from the animal host. Thus, dispersing the repellent into the air or dispersing the liquid as a liquid mist or fine dust will permit the repellent to fall on or be collected on the desired surface of the host. Likewise, directly spreading of a liquid/semi-solid/solid repellent on the host is an effective method of contacting the surface of the host with an effective amount of the repellent.

In formulating an insect repellent in accordance with this invention, it may be desirable to blend more than one of the compounds hereof together in a composition, which includes the possibility of blending together more than one isomer of a particular compound. It may also be desirable to formulate an insect repellent by combining one or more compounds of this invention to form a composition with a fugitive vehicle for application in the form of a spray.

A carrier useful for forming a composition in this invention can be any one of a variety of commercially available organic and inorganic liquid, solid, or semi-solid carriers or carrier formulations usable in formulating skin or insect repellent products. When formulating a skin product or topical insect repellent, it is preferred to select a dermatologically acceptable carrier. For example the carrier may include silicone, petrolatum, lanolin or many of several other well known carrier components. Examples of organic liquid carriers include liquid aliphatic hydrocarbons (e.g., pentane, hexane, heptane, nonane, decane and their analogs) and liquid aromatic hydrocarbons. Examples of other liquid hydrocarbons include oils produced by the distillation of coal and the distillation of various types and grades of petrochemical stocks, including kerosene oils which are obtained by fractional distillation of petroleum. Other petroleum oils include those generally referred to as agricultural spray oils (e.g., the so-called light and medium spray oils, consisting of middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid carriers can include liquid terpene hydrocarbons and terpene alcohols such as alpha-pinene, dipentene, terpineol, and the like.

Other carriers include silicone, petrolatum, lanolin, liquid hydrocarbons, agricultural spray oils, paraffin oil, tall oils, liquid terpene hydrocarbons and terpene alcohols, aliphatic and aromatic alcohols, esters, aldehydes, ketones, mineral oil, higher alcohols, finely divided organic and inorganic solid materials. In addition to the above-mentioned liquid hydrocarbons, the carrier can contain conventional emulsifying agents which can be used for causing the dihydronepetalactone compounds to be dispersed in, and diluted with, water for end-use application. Still other liquid carriers can include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Conventional aromatic and aliphatic esters, aldehydes and ketones can be used as carriers, and occasionally are used in combination with the above-mentioned alcohols. Still other liquid carriers include relatively high-boiling petroleum products such as mineral oil and higher alcohols (such as cetyl alcohol). Additionally, conventional or so-called "stabilizers" (e.g., tert-butyl sulfinyl dimethyl dithiocarbonate) can be used in conjunction with, or as a component of, the carrier or carriers comprising the compositions of the present invention.

Further, it may also be desirable to combine one or more compounds of this invention with one or more other types of insect repellents in a composition to achieve some particular beneficial effect as may result from such a combination. Suitable other insect repellents combinable for such purpose include but are not limited to DHN, benzil, benzyl benzoate, 2,3,4,5-bis(butyl-2-ene)tetrahydrofurfural, butoxypolypropylene glycol, N-butylacetanilide, normal-butyl-6,6-dimethyl-5,6-dihydro-1,4-pyrone-2-carboxylate, dibutyl adipate, dibutyl phthalate, di-normal-butyl succinate, N,N-diethyl-meta-toluamide, dimethyl carbate, dimethyl phthalate, 2-ethyl-2-butyl-1,3-propanediol, 2-ethyl-1,3-hexanediol, di-normal-propyl isocinchomeronate, 2-phenylcyclohexanol, p-methane-3,8-diol, and normal-propyl N,N-diethylsuccinamate.

In addition to the compound of Formula V, an insect repellent composition may also include one or more essential oils and/or active ingredients of essential oils. "Essential oils" are defined as any class of volatile oils obtained from plants possessing the odor and other characteristic properties of the plant. Examples of useful essential oils include: almond bitter oil, anise oil, basil oil, bay oil, caraway oil, cardamom oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronellal, methyl salicylate, ethyl salicylate, propyl salicylate, citronellol, safrole, and limonene.

The insects that may be repelled by the compounds of this invention may include any member of a large group of invertebrate animals characterized, in the adult state (non-adult insect states include larva and pupa) by division of the body into head, thorax, and abdomen, three pairs of legs, and, often (but not always) two pairs of membranous wings. This definition therefore includes a variety of biting insects [e.g. ants, bees, chiggers, fleas, black flies, green head flies, stable flies, horn flies (haematobia irritans), mosquitoes, ticks, wasps], wood-boring insects (e.g. termites), noxious insects (e.g. houseflies, cockroaches, lice, roaches, wood lice), and household pests (e.g. flour and bean beetles, dust mites, moths, silverfish, weevils). A host from which it may be desired to repel an insect may include any plant or animal (including humans) affected by insects. Typically, hosts are considered to be insect-acceptable food sources or insect-acceptable habitats.

In another embodiment, a compound may be used as a fragrance compound or in a fragrance composition, and be applied in a topical manner to human or animal skin or hair to impart a pleasing fragrance, as in skin lotions and perfumes.

Particularly because of the pleasant aroma associated with the compounds hereof, a further embodiment of this invention is one in which one or more compounds are formulated into a composition for use as a product that is directed to other fundamental purposes. The fragrance and/or insect repellency of these products will be enhanced by the presence therein of compound(s) of this invention. Included among such products (but not thereto limited) are colognes, lotions, sprays, creams, gels, ointments, bath and shower gels, foam products (e.g., shaving foams), makeup, deodorants, shampoo, hair lacquers/hair rinses, and personal soap compositions (e.g., hand soaps and bath/shower soaps). The compound(s) may of course be incorporated into such products simply to impart a pleasing aroma. Any means of incorporation such as is practiced in the art is satisfactory.

A corresponding aspect of the wide variety of products discussed above is a further alternative embodiment of this invention, which is a process for fabricating a composition of matter, a topical treatment for skin, or an article of manufacture, by providing as the composition, or incorporating into the composition, skin treatment or article, a compound of Formula V, or a mixture of the stereoisomers thereof. Such products, and the method and process described above, illustrate the use of a 3-substituted DHN as a fragrance compound or perfume, or in a fragrance composition or formulation, or in an article of manufacture.

A composition containing compound(s) of this invention prepared as an insect repellent, fragrance product, or other personal care product may also contain other therapeutically or cosmetically active adjuvants or ingredients as are typical in the personal care industry. Examples of these include fungicides, sunscreening agents, sunblocking agents, vitamins, tanning agents, plant extracts, anti-inflammatory agents, anti-oxidants, radical scavenging agents, retinoids, alpha-hydroxy acids, antiseptics, antibiotics, antibacterial agents, antihistamines; adjuvants such as thickeners, buffering agents, chelating agents, preservatives, gelling agents, stabilizers, surfactants, emollients, coloring agents, aloe vera, waxes, and penetration enhancers; and mixtures of any two or more thereof. The composition may also contain one or more carriers such as disclosed in US 2003/0191047 and/or WO 03/079786.

The amount of a compound of this invention contained in a composition will generally not exceed about 80% by weight based on the weight of the final product, however, greater amounts may be utilized in certain applications and this amount is not limiting. More preferably, a suitable amount of a compound will be at least about 0.001% by weight and preferably about 0.01% up to about 50% by weight; and more preferably, from about 0.01% to about 20% weight percent, based on the weight of the composition or article. Specific compositions will depend on the intended use.

In a further embodiment of this invention, compound(s) hereof is incorporated into an article to produce an insect repellent effect. Articles contemplated to fall within this embodiment include manufactured goods, including textile goods such as clothing, outdoor or military equipment, natural products such as lumber, or the leaves of insect vulnerable plants.

In another embodiment of this invention, compound(s) hereof is incorporated into an article to produce a fragrance pleasing to some humans, or compound(s) hereof is applied to the surface of an object to impart an odor thereto. The particular manner of application will depend upon the surface in question and the concentration required to impart the necessary intensity of odor.

Articles contemplated to fall within these embodiments include manufactured goods, including textile goods, air fresheners, candles, various scented articles, fibers, sheets, paper, paint, ink, clay, wood, furniture (e.g., for patios and decks), carpets, sanitary goods, plastics, polymers, and the like.

In another embodiment, the composition of the invention may serve as an attractant for pests, and be highly suitable for use in a trap.

The present invention is further described in, but not limited by, the following specific embodiments.

EXAMPLES 1–12

General Procedures

All reactions and manipulations were carried out in a standard laboratory fume hood open in standard laboratory glassware. Nepetalactones were obtained by steam distillation of commercially-available catnip oil from catmint, obtained from Berjé, (Bloomfield, N.J.). All inorganic salts and organic solvents, with the exception for anhydrous THF, were obtained from VWR Scientific. All other reagents used in the examples were obtained from Sigma-Aldrich Chemical (Milwaukee, Wis.) and used as received. Determination of pH was done with pHydrion paper from Micro Essential Laboratory. The 3-substituted dihydronepetalactone products were purified by column chromatography and characterized by NMR spectroscopy. NMR spectra were obtained on a Bruker DRX Advance (500 MHz $^1$H, 125 MHz $^{13}$C) using deuterated solvents obtained from Cambridge Isotope Laboratories.

The batches of nepetalic acid employed in Examples 1–12 were prepared according to the following procedures, although there was some variation in the amounts employed from batch to batch. A solution of cis-trans nepetalactone in 5 mL of tetrahydrofuran (THF) was treated with sodium hydroxide (1.0 g in 5 (mL of water) resulting in initially a two-phase mixture and then yellow solution. After 1 hour, the basic solution was extracted twice with fresh 20 mL aliquots of ethyl acetate. The aqueous layer from this extraction was acidified with 1N HCl drop-wise to pH=3 at which point it turned into a white heterogeneous mixture. The thus formed aqueous mixture was extracted twice with ethyl acetate and dried over anhydrous sodium sulfate. Removal of the solvent under vacuum resulted in a yellow oil which was triturated with petroleum ether (100 mL) and allowed to crystallize to a white solid on standing. The white solid was filtered, washed with cold petroleum ether (20 mL) and dried under high vacuum to afford nepetalic acid (1.9 g, 69%) with a melting point of 67° C. (lit. 71° C., *J. Org. Chem.* Vol. 46, No. 16, 1981 3302–3305). The absolute stereochemistry of the product was verified by single crystal analysis and was consistent with the structural representation depicted in structure of Formula VIa.

Example 1

Preparation of 3-phenyl-DHN ((3R,4R,4aR,7S,7aR)-4,7-dimethyl-3-phenylhexahydrocyclopenta[c]pyran-1(3H)-one)

A $C_{16}H_{20}O_2$
Mol. Wt.: 244.33

An oven-dried 100 mL three-necked round-bottomed flask was cooled to room temperature ("RT") under a steady stream of nitrogen. A solution of 500 mg of nepetalic acid in 10 mL anhydrous of THF was added to the flask and then cooled to 0° C. 363 mg of a suspension of 30% potassium hydride in mineral oil was weighed into another flask and washed with two 10 mL aliquots of hexane and removed by decantation once the solid settled. A further 10 mL aliquot of hexane was added to the solid and the resulting mixture was added to the three-necked round-bottomed flask in one portion. After twenty minutes, the resulting mixture was treated at 0° C. with phenylmagnesium bromide solution (4.1 mL of a 1M solution in THF) added drop-wise via syringe. After 30 minutes, the reaction warmed to room temperature and was stirred for 30 minutes. The mixture was acidified with 1N HCl drop-wise to pH=3.0 and extracted with three 10 mL aliquots of dichloromethane. The combined organic extracts were dried over anhydrous sodium sulfate. Removal of the solvent under vacuum resulted in a white solid (520 mg) with a melting point of 122–124° C. The product was recrystallized with ether and hexane to >95% purity according to NMR analysis. The absolute stereochemistry of product was verified by single crystal x-ray analysis and consistent with (3R,4R,4aR,7S,7aR)-4,7-dimethyl-3-phenylhexahydrocyclopenta[c]pyran-1(3H)-one represented by structure A.

Example 2

Preparation of 3-p-tolyl-DHN ((3R,4R,4aR,7S,7aR)-4,7-dimethyl-3-(4-methylphenyl)hexahydrocyclopenta[c]pyran-1(3H)-one)

B $C_{17}H_{22}O_2$
Mol. Wt.: 258.36

An oven-dried 100 mL three-necked round-bottomed flask was cooled to RT under a steady stream of nitrogen. A solution of 1.9 g of nepetalic acid in 40 mL of anhydrous THF was added to the flask and then cooled to 0° C. 407 mg of a suspension of 30% potassium hydride in mineral oil was weighed into another flask and washed with two 10 mL aliquots of hexane and removed by decantation once the solid settled. A further 10 mL aliquot of hexane was added to the solid and the resulting mixture was added to the three-necked round-bottomed flask in one portion. After twenty minutes, the resulting mixture was treated at 0° C. with p-tolylmagnesium bromide solution (15 mL of a 1M solution in THF) drop-wise via syringe. After 30 minutes, the reaction warmed to RT and was stirred for 30 minutes. The mixture was acidified with 1N HCl drop-wise to pH=3.0 and extracted with three 20 mL aliquots of dichloromethane. The combined organic extracts were dried over anhydrous sodium sulfate. Removal of the solvent under vacuum resulted in a white solid (2.8 g, >100%) with a melting point of 127–128° C. The product was recrystallized with ether and hexane to >95% purity according to NMR analysis. The absolute stereochemistry of product was verified by single crystal x-ray analysis and consistent with (3R,4R,4aR,7S,7aR)-4,7-dimethyl-3-(4-methylphenyl)hexahydrocyclopenta[c]pyran-1(3H)-one represented by structure B.

Example 3

Preparation of 3-m-tolyl-DHN ((3R,4R,4aR,7S,7aR)-4,7-dimethyl-3-(3-methylphenyl)hexahydrocyclopenta[c]pyran-1(3H)-one)

C

$C_{17}H_{22}O_2$
Mol. Wt.: 258.36

An oven-dried 100 mL three-necked round-bottomed flask was cooled to RT under a steady stream of nitrogen. A solution of 1.4 g of nepetalic acid in 30 mL of anhydrous THF was added to the flask and then cooled to 0° C. 304 mg of a suspension of 30% potassium hydride in mineral oil was weighed into another flask and washed with two 10 mL aliquots of hexane and removed by decantation once the solid settled. A fresh 10 mL aliquot of hexane was added to the solid and the resulting mixture was added to the three-necked round-bottomed flask in one portion. After twenty minutes, the resulting mixture was treated at 0° C. with m-tolylmagnesium bromide solution (15 mL of a 1M solution in THF) drop-wise via syringe. After 30 minutes, the reaction warmed to RT and was stirred for 30 minutes. The mixture was acidified with 1N HCl drop-wise to pH=3.0 and extracted with three 20 mL aliquots of dichloromethane (20 mL). The combined organic extracts were dried over anhydrous sodium sulfate. Removal of the solvent under vacuum resulted in a yellow oil (1.7 g). The product was purified by column chromatography using silica gel eluting with hexane followed by ethyl acetate. 0.66 g of purified products of (3R,4R,4aR,7S,7aR)-4,7-dimethyl-3-(3-methylphenyl) hexahydrocyclopenta[c]pyran-1(3H)-one was obtained as represented predominantly by the structure C.

Example 4

Preparation of 3-p-chlorophenyl-DHN ((3R,4R,4aR,7S,7aR)-3-(4-chlorophenyl)-4,7-dimethylhexahydrocyclopenta[c]pyran-1(3H)-one)

C$_{16}$H$_{19}$ClO$_2$
Mol. Wt.: 278.77

An oven-dried 100 mL three-necked round-bottomed flask was cooled to RT under a steady stream of nitrogen. A solution of 1.9 g of nepetalic acid in 40 mL of anhydrous THF was added to the flask and then cooled to 0° C. 407 mg of a suspension of 30% potassium hydride in mineral oil was weighed into another flask and washed with two 10 mL aliquots of hexane and removed by decantation once the solid settled. A fresh 10 mL aliquot of hexane was added to the solid and the resulting mixture was added to the three-necked round-bottomed flask in one portion. After twenty minutes, the resulting mixture was treated at 0° C. with p-chlorophenylmagnesium bromide solution (15 mL of a 1M solution in THF) drop-wise via syringe. After 30 minutes, the reaction warmed to RT and was stirred for 30 minutes. The mixture was acidified with 1N HCl drop-wise to pH=3.0 and extracted with three 20 mL aliquots of dichloromethane. The combined organic extracts were dried over anhydrous sodium sulfate. Removal of the solvent under vacuum resulted in a white solid (1.82 g). The product was purified by column chromatography using silica gel eluting with hexane followed by ethyl acetate. 290 mg of purified products obtained as a crystalline solid with a melting point of 137–139° C. and NMR analysis of the product was consistent with the product (3R,4R,4aR,7S,7aR)-3-(4-chlorophenyl)-4,7-dimethylhexahydrocyclopenta[c]pyran-1(3H)-one represented in structure D.

Example 5

Preparation of 3-p-methoxyphenyl-DHN ((3R,4R,4aR,7S,7aR)-3-(4-methoxyphenyl)-4,7-dimethylhexahydrocyclopenta[c]pyran-1(3H)-one)<

C$_{17}$H$_{22}$O$_3$
Mol. Wt.: 274.35

An oven-dried 100 mL three-necked round-bottomed flask was cooled to RT under a steady stream of nitrogen. A solution of 1.9 g of nepetalic acid (1.9 g) in anhydrous THF (40 mL) was added to the flask and then cooled to 0° C. 407 mg of a suspension of 30% potassium hydride in mineral oil was weighed into another flask and washed with two 10 mL aliquots of hexane and removed by decantation once the solid settled. A fresh 10 mL aliquot of hexane was added to the solid and the resulting mixture was added to the three-necked round-bottomed flask in one portion. After twenty minutes, the resulting mixture was treated at 0° C. with p-methoxyphenylmagnesium bromide solution (30 mL of a 0.5 M solution in THF) drop-wise via syringe. After 30 minutes, the reaction warmed to RT and was stirred for 30 minutes. The mixture was acidified with 1N HCl drop-wise to pH=3.0 and extracted with three 20 mL aliquots of dichloromethane. The combined organic extracts were dried over anhydrous sodium sulfate. Removal of the solvent under vacuum resulted in a white solid (0.89 g). The product was purified by column chromatography using silica gel eluting with hexane followed by ethyl acetate. 214 mg of purified products obtained as a crystalline solid with a melting point of 125–126° C. and NMR analysis of the product was consistent with (3R,4R,4aR,7S,7aR)-3-(4-methoxyphenyl)-4,7-dimethylhexahydrocyclopenta[c]pyran-1(3H)-one as represented by the structure E.

Example 6

Preparation of 3-m-methoxyphenyl-DHN ((3R,4R,4aR,7S,7aR)-3-(3-methoxyphenyl)-4,7-dimethylhexahydrocyclopenta[c]pyran-1(3H)-one)

C$_{17}$H$_{22}$O$_3$
Mol. Wt.: 274.35

An oven-dried 100 mL three-necked round-bottomed flask was cooled to RT under a steady stream of nitrogen. A solution of 1.9 g of nepetalic acid in 40 mL of anhydrous THF was added to the flask and then cooled to 0° C. 407 mg of a suspension of 30% potassium hydride in mineral oil was weighed into another flask and washed with two 10 mL aliquots of hexane and removed by decantation once the solid settled. A fresh 10 mL aliquot of hexane was added to the solid and the resulting mixture was added to the three-necked round-bottomed flask in one portion. After twenty minutes, the resulting mixture was treated at 0° C. with m-methoxyphenylmagnesium bromide solution (15 mL of a 1M solution in THF) drop-wise via syringe. After 30 minutes, the reaction warmed to RT and was stirred for 30 minutes. The mixture was acidified with 1N HCl drop-wise to pH=3.0 and extracted with three 20 mL aliquots of dichloromethane (20 mL). The combined organic extracts were dried over anhydrous sodium sulfate. Removal of the solvent under vacuum resulted in a yellow oil (2.0 g). The product was purified by column chromatography using silica gel eluting with hexane followed by ethyl acetate. 0.466 g of purified products was obtained and NMR analysis of the product was consistent with (3R,4R,4aR,7S,7aR)-3-(3-methoxyphenyl)-4,7-dimethylhexahydrocyclopenta[c]pyran-1(3H)-one and represented by structure F.

Example 7

Preparation of 3-p-fluorophenyl-DHN ((3R,4R,4aR,7S,7aR)-3-(4-fluorophenyl)-4,7-dimethylhexahydrocyclopenta[c]pyran-1 (3H)-one)

G $C_{16}H_{19}FO_2$
Mol. Wt.: 262.32

An oven-dried 100 mL three-necked round-bottomed flask was cooled to RT under a steady stream of nitrogen. A solution of 1.9 g of nepetalic acid in 40 mL of anhydrous THF was added to the flask and then cooled to 0° C. 407 mg of a suspension of 30% potassium hydride in mineral oil was weighed into another flask and washed with two 10 mL aliquots of hexane and removed by decantation once the solid settled. A fresh 10 mL aliquot of hexane was added to the solid and the resulting mixture was added to the three-necked round-bottomed flask in one portion. After twenty minutes, the resulting mixture was treated at 0° C. with p-methoxyphenylmagnesium bromide solution (15 mL of a 1.0 M solution in THF) drop-wise via syringe. After 30 minutes, the reaction warmed to RT and was stirred for 30 minutes. The mixture was acidified with 1N HCl drop-wise to pH=3.0 and extracted with three 20 mL aliquots of dichloromethane. The combined organic extracts were dried over anhydrous sodium sulfate. Removal of the solvent under vacuum resulted in a white solid (2.04 g). The product was purified by column chromatography using silica gel eluting with hexane followed by ethyl acetate. 405 mg of purified products were obtained as a crystalline solid with a melting point of 154–156° C. and NMR analysis of the product was consistent with (3R,4R,4aR,7S,7aR)-3-(4-fluorophenyl)-4,7-dimethylhexahydrocyclopenta[c]pyran-1(3H)-one as represented by structure G.

Example 8

Preparation of 3-(p-fluoro-m-methyl)-phenyl-DHN ((3R,4R,4aR,7S,7aR)-3-(4-fluoro-3-methylphenyl)-4,7-dimethylhexahydrocyclopenta[c]pyran-1(3H)-one)

H $C_{17}H_{21}FO_2$
Mol. Wt.: 276.35

An oven-dried 100 mL three-necked round-bottomed flask was cooled to RT under a steady stream of nitrogen. A solution of 1.9 g of nepetalic acid in 40 mL of anhydrous THF was added to the flask and then cooled to 0° C. 407 mg of a suspension of 30% potassium hydride in mineral oil was weighed into another flask and washed with two 10 mL aliquots of hexane and removed by decantation once the solid settled. A fresh 10 mL aliquot of hexane was added to the solid and the resulting mixture was added to the three-necked round-bottomed flask in one portion. After twenty minutes, the resulting mixture was treated at 0° C. with m-methoxyphenylmagnesium bromide solution (15 mL of a 1M solution in THF) drop-wise via syringe. After 30 minutes, the reaction warmed to RT and was stirred for 30 minutes. The mixture was acidified with 1N HCl drop-wise to pH=3.0 and extracted with three 20 mL aliquots of dichloromethane. The combined organic extracts were dried over anhydrous sodium sulfate. Removal of the solvent under vacuum resulted in a yellow oil (3.2 g). The product was purified by column chromatography using silica gel eluting with hexane followed by ethyl acetate. 0.616 g of purified product was obtained and NMR analysis of the product was consistent with (3R,4R,4aR,7S,7aR)-3-(4-fluoro-3-methylphenyl)-4,7-dimethylhexahydrocyclopenta[c]pyran-1(3H)-one as represented by structure H.

Example 9

Preparation of 3-methyl-DHN ((3S,4R,4aR,7S,7aR)-3,4,7-trimethylhexahydrocyclopenta[c]pyran-1(3H)-one, and (3R,4R,4aR,7S,7aR)-3,4,7-trimethylhexahydrocyclopenta[c]pyran-1(3H)-one)

I $C_{11}H_{18}O_2$
Mol. Wt.: 182.26

An oven-dried 100 mL three-necked round-bottomed flask was cooled to RT under a steady stream of nitrogen. A solution of 2.13 g of nepetalic acid in 40 mL of anhydrous THF (40 mL) was added to the flask and then cooled to 0° C. 1.40 g of a suspension of 30% potassium hydride in mineral oil was weighed into another flask and washed with two 20 mL aliquots of hexane and removed by decantation once the solid settled. A further 20 mL aliquot of hexane was added to the solid and the resulting mixture was added to the three-necked round-bottomed flask in one portion. After twenty minutes, the resulting mixture was treated at 0° C. with methylmagnesium chloride solution (5.8 mL of 3M solution in THF) drop-wise via syringe. After 30 minutes, the reaction warmed to RT and was stirred for 30 minutes. The mixture was acidified with 1N HCl drop-wise to pH=3.0 and extracted with three 40 mL aliquots of dichloromethane. The combined organic extracts were dried over anhydrous sodium sulfate. Removal of the solvent under vacuum resulted in a pale oil (1.88 g). Purification of the crude reaction product was carried out by column chromatography using silica gel eluting with hexane followed by ethyl acetate. The 3-methyl-dihydronepetalactone diastereomers were not separable by this method. 0.682 g of purified product was obtained and NMR analysis of the product was consistent with the (3S,4R,4aR,7S,7aR)-3,4,7-trimethyl-hexahydrocyclopenta[c]pyran-1(3H)-one and (3R,4R,4aR,7S,7aR)-3,4,7-trimethylhexahydrocyclopenta[c]pyran-1(3H)-one as represented by the diastereomeric structure I.

Example 10

Preparation of 3-ethyl-DHN ((3R,4R,4aR,7S,7aR)-3-ethyl-4,7-dimethylhexahydrocyclopenta[c]pyran-1(3H)-one, and (3S,4R,4aR,7S,7aR)-3-ethyl-4,7-dimethylhexahydrocyclopenta[c]pyran-1(3H)-one)

J $C_{12}H_{20}O_2$
Mol. Wt.: 196.29

An oven-dried 100 mL three-necked round-bottomed flask was cooled to RT under a steady stream of nitrogen. A solution of 1.84 g of nepetalic acid in 40 mL of anhydrous THF was added to the flask and then cooled to 0° C. 441 mg of a suspension of 30% potassium hydride in mineral oil was weighed into another flask and washed with two 20 mL aliquots of hexane and removed by decantation once the solid settled. A further 20 mL aliquot of hexane was added to the solid and the resulting mixture was added to the three-necked round-bottomed flask in one portion. After twenty minutes, the resulting mixture was treated at 0° C. with ethylmagnesium chloride solution (15 mL of 1.0 M solution in THF) drop-wise via syringe. After 30 minutes, the reaction warmed to RT and was stirred for 30 minutes. The mixture was acidified with 1N HCl drop-wise to pH=3.0 and extracted with three 20 mL aliquots of dichloromethane. The combined organic extracts were dried over anhydrous sodium sulfate. Removal of the solvent under vacuum resulted in a pale oil (1.21 g). Purification of the crude reaction product was carried out by column chromatography using silica gel eluting with hexane followed by ethyl acetate. The 3-ethyl-dihydronepetalactone diastereomers were not separable by this method. 0.253 g of purified product was obtained and NMR analysis of the product was consistent with (3R,4R,4aR,7S,7aR)-3-ethyl-4,7-dimethyl-hexahydrocyclopenta[c]pyran-1(3H)-one and (3S,4R,4aR,7S,7aR)-3-ethyl-4,7-dimethylhexahydrocyclopenta[c]pyran-1(3H)-one as represented by the diastereomeric structure J.

Example 11

Preparation of 3-n-propyl-DHN ((3S,4R,4aR,7S,7aR)-4,7-dimethyl-3-propylhexahydrocyclopenta[c]pyran-1(3H)-one, and (3R,4R,4aR,7S,7aR)-4,7-dimethyl-3-propylhexahydrocyclopenta[c]pyran-1(3H)-one)

K $C_{13}H_{22}O_2$
Mol. Wt.: 210.31

An oven-dried 100 mL three-necked round-bottomed flask was cooled to RT under a steady stream of nitrogen. A solution of 1.84 g of nepetalic acid in 40 mL of anhydrous THF was added to the flask and then cooled to 0° C. 441 mg of a suspension of 30% potassium hydride in mineral oil was weighed into another flask and washed with two 20 mL aliquots of hexane and removed by decantation once the solid settled. A further 20 mL aliquot of hexane was added to the solid and the resulting mixture was added to the three-necked round-bottomed flask in one portion. After twenty minutes, the resulting mixture was treated at 0° C. with n-propylmagnesium chloride solution (15 mL of 1.0 M solution in THF) drop-wise via syringe. After 30 minutes, the reaction warmed to RT and was stirred for 30 minutes. The mixture was acidified with 1N HCl drop-wise to pH=3.0 and extracted with three 20 mL aliquots of dichloromethane. The combined organic extracts were dried over anhydrous sodium sulfate. Removal of the solvent under vacuum resulted in a pale oil (1.26 g). Purification of the crude reaction product was carried out by column chromatography using silica gel eluting with hexane followed by ethyl acetate. The 4-n-propyl-dihydronepetalactone diastereomers were not separable by this method. 0.713 g of purified product was obtained and NMR analysis of the product was consistent with (3S,4R,4aR,7S,7aR)-4,7-dimethyl-3-propylhexahydrocyclopenta[c]pyran-1(3H)-one and (3R,4R,4aR,7S,7aR)-4,7-dimethyl-3-propylhexahydrocyclopenta[c]pyran-1(3H)-one as represented by the diastereomeric structure K.

Example 12

Preparation of 3-methyl-DHN ((3S,4R,4aR,7S,7aR)-3,4,7-trimethylhexahydrocyclopenta[c]pyran-1(3H)-one, and (3R,4R,4aR,7S,7aR)-3,4,7-trimethyl-hexahydrocyclopenta[c]pyran-1(3H)-one)

L $C_{11}H_{18}O_2$
Mol. Wt.: 182.26

An oven-dried 3 liter three-necked round-bottomed flask was cooled to RT under a steady stream of nitrogen. A solution of 55.3 g of nepetalic acid in 800 mL of anhydrous THF was added to the flask and then cooled to 0° C. The solution was treated with methylmagnesium bromide solution (200 mL 3.0M solution in ether) drop-wise via syringe. After 30 minutes, the reaction warmed to RT and was stirred for 30 minutes. The mixture was acidified with 1N HCl drop-wise to pH=3.0 and extracted with three 200 mL aliquots of dichloromethane. The combined organic extracts were dried over anhydrous sodium sulfate. Removal of the solvent under vacuum resulted in a pale oil (51.0 g). Purification of the crude reaction product was carried out by column chromatography using silica gel eluting with hexane followed by ethyl acetate. The 3-methyl-dihydronepetalactone diastereomers were not separable by this method. 21.77 g of purified product was obtained and NMR analysis of the product was consistent with (3S,4R,4aR,7S,7aR)-3,4,7-trimethylhexahydrocyclopenta[c]pyran-1(3H)-one and (3R,4R,4aR,7S,7aR)-3,4,7-trimethylhexahydrocyclopenta[c]pyran-1(3H)-one as represented by the diastereomeric structure L.

EXAMPLES 13–19

The products of Examples 1–12 were evaluated for the insect repellency against *Aedes aegypti* mosqutioes in the in vitro Gupta box landing assay. In this method a chamber contained 5 wells, each covered by a Baudruche (animal intestine) membrane. Each well was filled with bovine blood, containing sodium citrate (to prevent clotting) and ATP (72 mg ATP disodium salt per 26 ml of blood), and heated to 37° C. A volume of 25 μl of isopropyl alcohol (IPA) containing one test specimen or control was applied to each membrane. The concentrations were all 1% in IPA except where otherwise indicated. Controls were either neat IPA an untreated membrane surface, or a membrane surface treated with a 1% solution of DEET.

After 5 min, approximately 250 4-day-old female *Aedes aegypti* mosquitoes were introduced into the chamber. The number of mosquitoes probing the membranes for each treatment was recorded at 2 min intervals over 20 min. Each datum represents the mean of three replicate experiments.

Example 13

Figure 1:
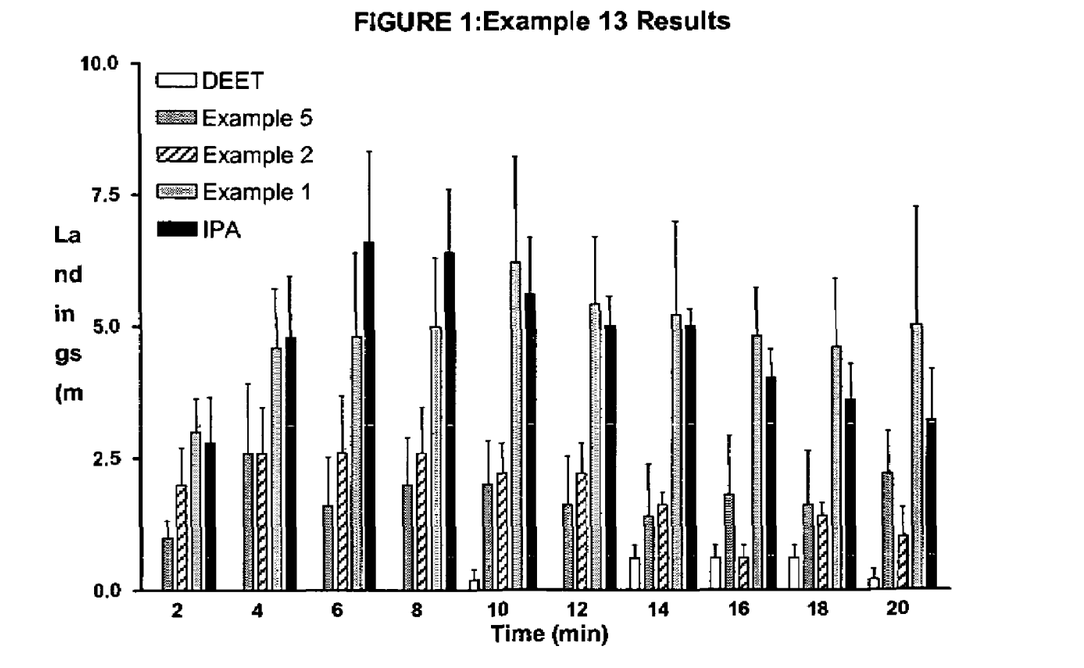
FIGS. 1–5 represent the results of testing the indicated compounds of the present invention against the indicated controls for their effect on the probing behavior of *Aedes aegypti* mosquitoes in the in vitro Gupta box landing assay procedure, described hereinbelow. The horizontal scale shows time in minutes, and the vertical scale shows mean number of landings of mosquitoes.

Specimens prepared in Example 1, Example 2, and Example 5 were evaluated according to the test method above described. Results are shown in FIG. 1.

Example 14

Figure 2:
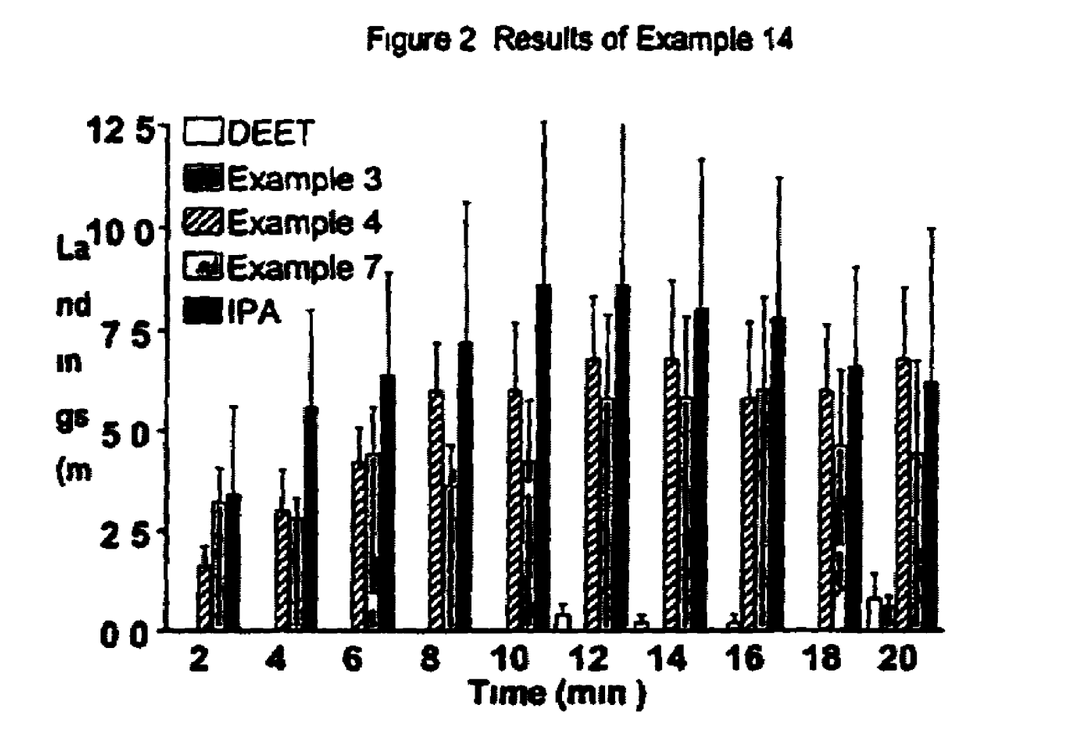

Specimens prepared in Example 3, Example 4, and Example 7 were evaluated according to the test method above described. Results are shown in FIG. 2.

Example 15

Figure 3:
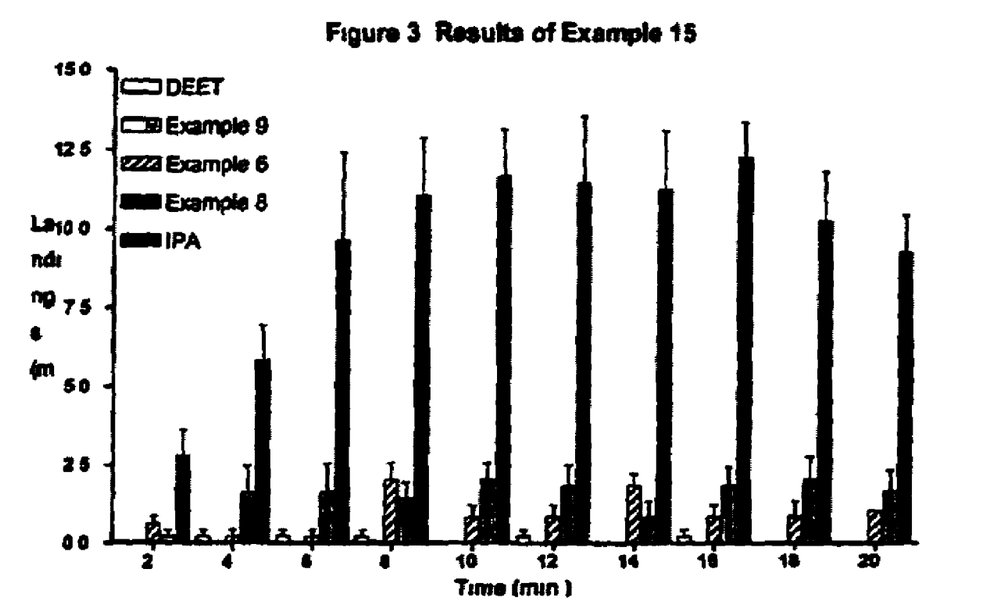

Specimens prepared in Example 6, Example 8, and Example 9 were evaluated according to the test method above described. Results are shown in FIG. 3.

Example 16

Figure 4:
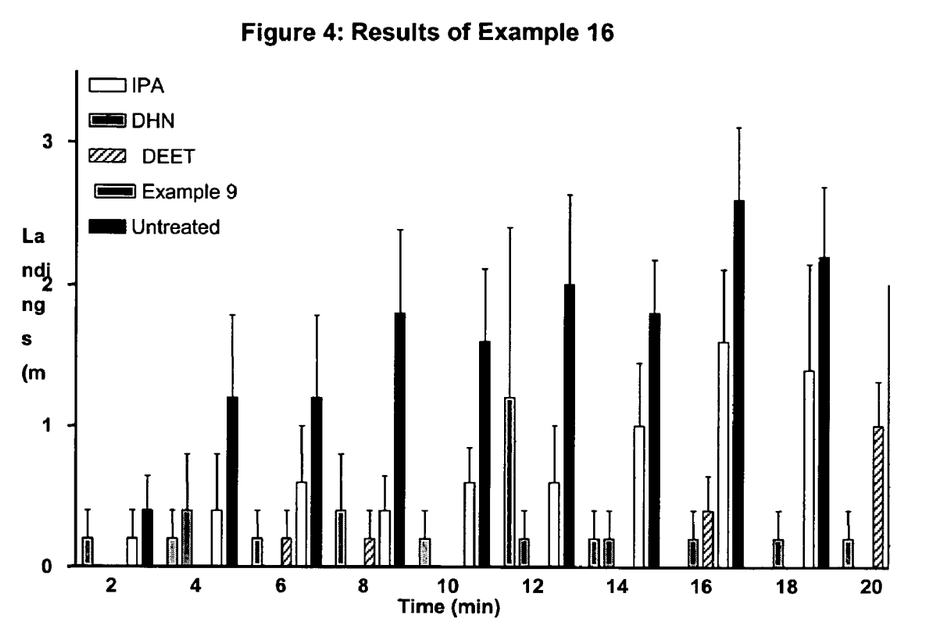

Following the procedures of Examples 13–15, a 0.5% solution of the compound of Example 9 in IPA was deposited upon the test membranes, along with 0.5% solutions of DEET and DHN. Both untreated membrane and membrane treated with neat IPA were additional controls. The DHN was prepared from trans, cis nepetalctone by hydrogenation according to the teachings of Hallahan. Results are shown in FIG. 4.

Example 17

Figure 5:
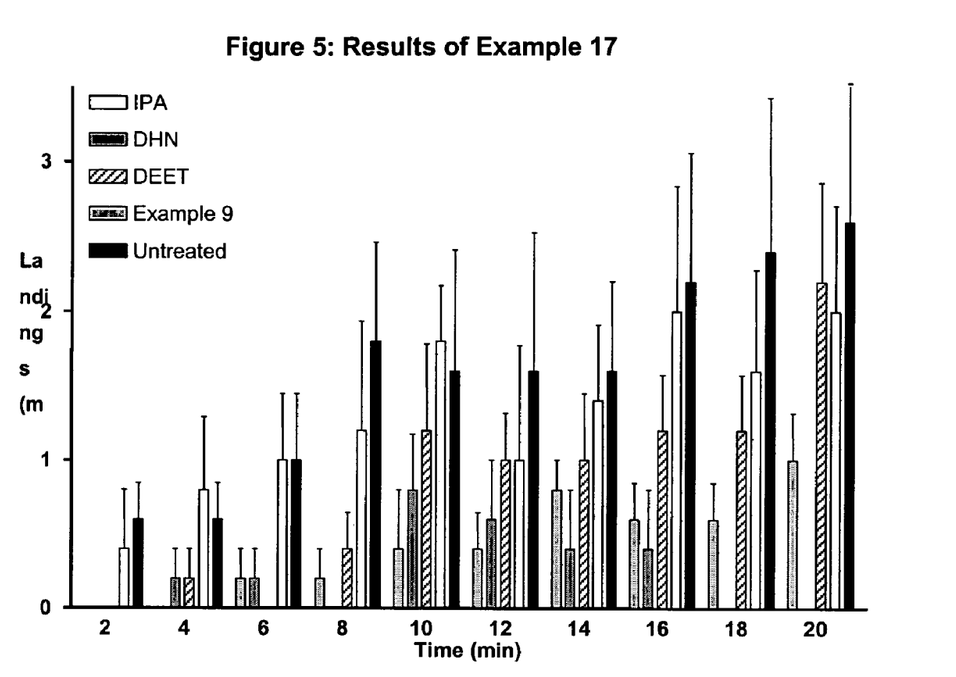

Following the procedures of Examples 13–15, a 0.1% solution of the compound of Example 9 in IPA was deposited upon the test membranes, along with 0.1% solutions of DEET and DHN. Both untreated membrane and membrane treated with neat IPA were additional controls. The DHN was prepared from trans, cis nepetalctone by hydrogenation according to the teachings of Hallahan. Results are shown in FIG. 5.

The invention claimed is:

1. A compound represented schematically by the structure of Formula V wherein R is alkyl or aryl:

V

2. A compound according to claim 1 wherein R is $C_1$ to $C_{20}$ alkyl.

3. A compound according to claim 1 wherein R is $C_6$ to $C_{20}$ aryl.

4. A compound according to claim 1 wherein R is selected from the group consisting of methyl, ethyl, propyl, phenyl, tolyl, alkoxy-phenyl and halo-phenyl.

5. A compound according to claim 1 which is a single stereoisomer of a single compound.

6. A compound according to claim 1 which is a mixture of stereoisomers of a single compound.

7. A compound according to claim 1 which is selected from one or more members of the group consisting of (3R,4R,4aR,7S,7aR)-4,7-dimethyl-3-(4-methylphenyl)
hexahydrocyclopenta[c]pyran-1(3H)-one;
(3R,4R,4aR,7S,7aR)-3-(3-methoxyphenyl)-4,7-dimethyl-
hexahydrocyclopenta[c]pyran-1(3H)-one;
(3S,4R,4aR,7S,7aR)-3,4,7-trimethylhexahydrocyclopenta
[c]pyran-1(3H)-one; and
(3R,4R,4aR,7S,7aR)-3,4,7-trimethylhexahydrocyclopenta
[c]pyran-1(3H)-one.

8. A process for preparing a compound according to claim 1 comprising contacting nepetalic acid with a base, and with a Grignard reagent.

9. A process according to claim 8 wherein the base is a non-aqueous base.

10. A process according to claim 8 wherein the base is a Grignard reagent.

11. A process according to claim 8 wherein the Grignard reagent is an alkyl Grignard reagent.

12. A process according to claim 8 wherein the Grignard reagent is an aryl Grignard reagent.

13. A process according to claim 8 further comprising a step of providing nepetalic acid by the hydration of nepetalactone.

14. A process for preparing a compound according to claim 1 comprising contacting nepetalic acid with a Grignard reagent, wherein the amount of Grignard reagent per mole of nepetalic acid is greater than 1.

15. A process according to claim 14 wherein the Grignard reagent is an alkyl Grignard reagent.

16. A process according to claim 14 wherein the Grignard reagent is an aryl Grignard reagent.

17. A process according to claim 14 further comprising a step of providing nepetalic acid by the hydration of nepetalactone.

18. A composition of matter comprising the compound of claim 1.

19. A method of repelling one or more insects comprising exposing the insect(s) to a compound according to claim 1.

20. A method according to claim 19 wherein the insect(s) are selected from one or more members of the group consisting of biting flies, chiggers, fleas, mosquitoes, ticks and lice.

* * * * *